United States Patent [19]

Blaser et al.

[11] Patent Number: 4,785,089
[45] Date of Patent: Nov. 15, 1988

[54] NOVEL SULFONIC ACID ESTERS AND THEIR PREPARATION

[75] Inventors: Hans-Ulrich Blaser, Ettingen; Hans-Peter Jalett, Basle, both of Féd. Rep. of Germany; Gottfried Sedelmeier, Schallstadt, Fed. Rep. of Germany

[73] Assignee: Ciba-Geigy Corporation, Ardsley, N.Y.

[21] Appl. No.: 869,799

[22] Filed: Jun. 2, 1986

[30] Foreign Application Priority Data

Jun. 13, 1985 [CH] Switzerland ............... 2501/85

[51] Int. Cl.⁴ ............... C07C 143/68; C07C 99/100; C07D 223/16; C07D 31/55; C07D 31/36; C07D 31/335; C07D 31/255; C07B 53/00
[52] U.S. Cl. .................... 540/523; 558/52; 549/350; 549/362; 549/366; 549/440; 549/447
[58] Field of Search ............ 558/52; 540/523; 514/464, 252, 450, 213, 517; 549/440, 447, 350, 360, 362

[56] References Cited

U.S. PATENT DOCUMENTS

| | | | |
|---|---|---|---|
| 4,329,487 | 5/1982 | Yoshio et al. | 560/60 |
| 4,473,575 | 9/1984 | Watthey | 540/523 |

FOREIGN PATENT DOCUMENTS

| | | | |
|---|---|---|---|
| 050850 | 5/1982 | European Pat. Off. | 548/491 |
| 072352 | 2/1983 | European Pat. Off. | 540/523 |
| 081320 | 6/1983 | European Pat. Off. | 558/52 |
| 126986 | 12/1984 | European Pat. Off. | 558/52 |
| 134392 | 3/1985 | European Pat. Off. | 558/52 |
| 35060 | 3/1980 | Japan . | |

OTHER PUBLICATIONS

Effenberger, Angew. Chem. 95: p. 50 [1983].
Urbach and Henning, Tetrahedron Letters 25: pp. 1143–1146 [1983].

*Primary Examiner*—Robert T. Bond
*Attorney, Agent, or Firm*—Irving M. Fishman

[57] ABSTRACT

The invention relates to novel sulfonic acid esters of formula I

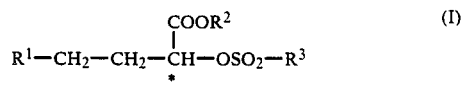

wherein $R^1$ is $C_5$–$C_6$cycloalkyl which is unsubstituted or substituted by $C_1$–$C_7$alkyl, unsubstituted or substituted phenyl, $R^2$ is $C_1$–$C_7$alkyl, $R^3$ is phenyl which is substituted by halogen or nitro, and the asterisk denotes a carbon atom that is either present in the preponderant number of molecules in the S configuration or in the preponderant number of molecules in the R configuration.

These compounds can be prepared by enantio-selective reduction of 4—$R^1$—substituted α-oxobutyric acid compounds and subsequent conversion of the resultant α-hydroxy group into the —$OSO_2$—$R^3$ group. The compounds of formula I are suitable intermediates for the preparation of ACE inhibitors or precursors thereof.

25 Claims, No Drawings

NOVEL SULFONIC ACID ESTERS AND THEIR PREPARATION

The present invention relates to novel sulfonic acid esters, to the preparation thereof, and to the use of these compounds as intermediates for the preparation of ACE inhibitors or their precursors.

The novel sulfonic acid esters have the formula

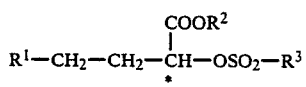

where $R^1$ is $C_5$–$C_6$cycloalkyl which is unsubstituted or substituted by $C_1$–$C_7$alkyl or is unsubstituted or substituted phenyl, $R^2$ is $C_1$–$C_7$alkyl, $R^3$ is phenyl which is substituted by halogen or nitro, and the asterisk denotes a carbon atom that is present either in the preponderant number of molecules in the S configuration or in the preponderant number of molecules in the R configuration.

A phenyl radical $R^1$ may carry substituents selected from the group consisting of $C_1$–$C_7$alkyl, e.g. methyl, hydroxy, $C_1$–$C_7$alkoxy, e.g. methoxy, $C_1$–$C_7$alkanoyloxy, e.g. acetoxy, fluorine, $C_1$–$C_7$alkylenedioxy, e.g. ethylenedioxy, amino, $C_1$–$C_7$alkylamino, e.g. methylamino, di($C_1$–$C_7$)alkylamino, e.g. dimethylamino, $C_1$–$C_7$alkanoylamino, e.g. acetylamino, carbamoyl, $C_1$–$C_7$alkylcarbamoyl, e.g. methylcarbamoyl, di($C_1$–$C_7$)alkylcarbamoyl, e.g. dimethylcarbamoyl, $C_1$–$C_7$alkylsulfonylamino, e.g. methyl- or ethylsulfonylamino, sulfamoyl, $C_1$–$C_7$alkylsulfamoyl, e.g. methylsulfamoyl, di($C_1$–$C_7$)alkylsulfamoyl, e.g. dimethylsulfamoyl, $C_1$–$C_7$haloalkyl, e.g. trifluoromethyl, $C_1$–$C_7$hydroxyalkyl, e.g. hydroxymethyl, and $C_1$–$C_7$aminoalkyl, e.g. aminomethyl or 2-aminoethyl.

Throughout this specification, the general terms employed have the meanings as defined below and the prefix "$C_1$–$C_7$" denotes organic radicals containing 1 to 7, preferably 1 to 4, carbon atoms.

$C_1$–$C_7$Alkyl is e.g. methyl, ethyl, propyl, isopropyl, butyl or tert-butyl, but may also be pentyl, hexyl or heptyl.

$C_1$–$C_7$Alkoxy is e.g. methoxy, ethoxy, propoxy, isopropoxy or one of the four butoxy isomers.

$C_1$–$C_7$Alkanoyl is e.g. formyl, acetyl, propionyl or butyryl, and also isobutyryl or pivaloyl.

$C_1$–$C_7$Alkanoyloxy is e.g. acetoxy, propionyloxy, butyryloxy, and may also be formyloxy or pivaloyloxy.

$C_5$–$C_6$Cycloalkyl is cyclopentyl or cyclohexyl. $C_1$–$C_7$Alkyl-substituted $C_5$–$C_6$cycloalkyl is e.g. ethylcyclohexyl or methylcyclohexyl such as 4-methylcyclohexyl.

Aryl is e.g. naphthyl or, preferably, phenyl.

1-$C_1$–$C_7$Aralkyl is e.g. 1-naphthylethyl, benzyl or, preferably, 1-phenylethyl.

Halogen is e.g. fluorine or iodine, but is preferably chlorine or bromine.

$C_1$–$C_7$Alkylenedioxy is e.g. ethylenedioxy, 1,3-propylenedioxy, 2,3-butylenedioxy or 1,3-(2,2-dimethyl)-propoylenedioxy.

$C_1$–$C_7$Alkylamino or di($C_1$–$C_7$)alkylamino ie e.g. methylamino, dimethylamino, ethylamino, diethylamino, propylamino, isopropylamino or butylamino.

$C_1$–$C_7$Alkanoylamino is e.g. acetylamino or propionylamino and may also be formylamino.

$C_1$–$C_7$Alkylcarbamoyl or di($C_1$–$C_7$)alkylcarbamoyl is e.g. methylcarbamoyl, dimethylcarbamoyl, ethylcarbamoyl, diethylcarbamoyl, propylcarbamoyl or butylcarbamoyl.

$C_1$–$C_7$Alkylsulfonylamino is e.g. methylsulfonylamino, ethylsulfonylamino or propylsulfonylamino.

$C_1$–$C_7$Alkylsulfamoyl or di($C_1$–$C_7$)alkylsulfamoyl is e.g. methylsulfamoyl, dimethylsulfamoyl, ethylsulfamoyl, diethylsulfamoyl, propylsulfamoyl or butylsulfamoyl.

$C_1$–$C_7$Haloalkyl is e.g. halomethyl such as trifluoromethyl, or 2-chloroethyl.

$C_1$–$C_7$Hydroxyalkyl is e.g. hydroxymethyl or 1-hydroxymethyl or, preferably, 2-hydroxyethyl.

$C_1$–$C_7$Aminoalkyl is e.g. aminomethyl or 1- or 2-aminoethyl.

$R^3$ as nitro-substituted phenyl is e.g. mono- or dinitrophenyl such as 2-, 3- or 4-nitrophenyl or 2,4-dinitrophenyl.

$R^3$ as halogen-substituted phenyl is phenyl which is substituted by 1 to 5 halogen atoms such as fluorine, chlorine or bromine and is for example bromophenyl, trichlorophenyl or pentafluorophenyl.

The asterisk denoting a carbon atom that is present in the preponderant number of molecules in the S configuration or in the preponderant number of molecules in the R configuration signifies that the compounds of formula I, with respect to said carbon atom, are obtained as substantially pure enantiomers and not as racemates. The term "substantially pure" means, with respect to formula I, a ratio of enantiomers that differs from the equimolar ratio of a racemate such that said ratio is at least 90:10, preferably at least 95:5 and, most preferably, 98:2 to 100:0, with the R or S form predominating. In preferred compounds of formula I, the R-configuration in a ratio as defined above will predominate.

Preferred compounds of formula I are also those wherein $R^1$ is $C_5$–$C_6$cycloalkyl, phenyl or phenyl which is substituted by $C_1$–$C_7$-alkyl, hydroxy, $C_1$–$C_7$alkoxy, $C_1$–$C_7$alkanoyloxy, fluorine, trifluoromethyl or $C_1$–$C_7$alkylenedioxy, and $R^2$, $R^3$ and the asterisk have the meanings assigned to them above.

Further preferred compounds of formula I are those wherein $R^1$ is $C_5$–$C_6$cycloalkyl, phenyl or phenyl which is substituted by a number selected from $C_1$–$C_4$alkyl, hydroxy, $C_1$–$C_4$alkoxy or fluorine, $R^2$ is $C_1$–$C_4$alkyl, $R^3$ is 2-, 3- or 4-nitrophenyl, 2,4-dinitrophenyl or pentafluorophenyl, and the asterisk denotes a carbon atom that is present either in the preponderant number of molecules in the S configuration or in the preponderant number of molecules in the R configuration, with the R configuration being preferred.

Particularly preferred compounds of formula I are those wherein $R^1$ is cyclohexyl, phenyl, $C_1$–$C_4$alkylphenyl or $C_1$–$C_4$alkoxyphenyl, $R^2$ is $C_1$–$C_4$alkyl, $R^3$ is 4-nitrophenyl or 2,4-dinitrophenyl, and the asterisk denotes a carbon atom that is present in the preponderant number of molecules in the R-configuration.

The most preferred compounds of formula I are those wherein $R^1$ is phenyl, $R^2$ is $C_1$–$C_4$alkyl, $R^3$ is 4-nitrophenyl or 2,4-dinitrophenyl and the asterisk denotes a carbon atom that is present in the preponderant number of molecules in the R-configuration; and, among these compounds, first and foremost those wherein $R^2$ is ethyl.

The compounds of formula I can be prepared in a manner known per se by reacting an α-hydroxy ester of formula II

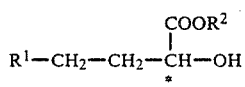 (II)

wherein $R^1$ and $R^2$ are as defined for formula I and the asterisk denotes a carbon atom that is present either in the preponderant number of molecules in the S configuration or in the preponderant number of molecules in the R configuration, with a compound that converts the —OH substituent into the radical of formula —OSO$_2$—$R^3$, wherein $R^3$ is as defined for formula I.

Compounds that convert the —OH substituent into the radical —OSO$_2$—$R^3$ are e.g. $R^3$-sulfonic acid anhydrides such as mixed anhydrides, for example with hydrohalic acids, i.e. $R^3$-sulfonyl halides, such as $R^3$-sulfonyl chlorides or bromides, as well as anhydrides of the respective $R^3$-sulfonic acids themselves, i.e. compounds of the type $R^3$—SO$_2$—O—SO$_2$—$R^3$. The reaction is advantageously carried out in an inert solvent as well as in the presence of a base. Examples of suitable solvents are halogenated hydrocarbons such as dichloromethane, chloroform or carbon tetrachloride, and also hydrocarbons such as toluene, benzene or hexane. Suitable bases are inorganic or organic bases, e.g. basic alkali metal salts or alkaline earth metal salt such as alkali metal carbonates, e.g. potassium carbonate, sodium carbonate, sodium bicarbonate, and also tertiary amines such as pyridine or trialkylamines, e.g. triethylamine.

The reaction is conveniently carried out in the temperature range from −50° to +110° C., if desired in an inert gas atmosphere, for example under nitrogen or argon.

The reaction course is stereochemically uniform such that the configuration at the carbon atom indicated by an asterisk is retained. Accordingly, the asterisk in formula II denotes a ratio of enantiomers as defined for formula I, but a ratio of enantiomers of at least 80:20, preferably of at least 85:15.

Starting compounds of formula II are known or can be prepared in a manner which is known per se. Numerous known preparatory methods (q.v. for example European patent application 126 986) such as the reduction of corresponding α-keto esters with Raney nickel and hydrogen or the acid saponification of corresponding α-hydroxy nitriles and subsequent esterification lead to racemic α-hydroxy esters which have to be separated in a subsequent additional step, e.g. via diastereoisomers, by chromatography or fractional crystallisation. This separation step entails the regular loss of at least 50% of the racemic mixture. There is consequently a need for a process that avoids such a wasteful separation of isomers.

Within the scope of the present invention it has been found that a known process for the asymmetrical reduction of certain α-keto esrters (q.v. for example U.S. Pat. No. 4,329,487 or Japanese published patent application No. 80 35 060) can be applied with good success to compounds of formula III

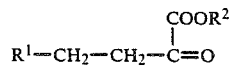 (III)

wherein $R^1$ and $R^2$ are as defined for formula I. A further object of the invention therefore resides in preparing a compound of formula I as defined above by enantio-selective reduction of a compound of formula III

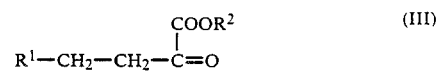 (III)

wherein $R^1$ and $R^2$ are as defined for formula I, in the presence of a platinum catalyst on a carrier as well as of a cinchona alkaloid, to a compound of formula II as defined above

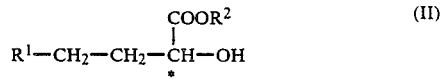 (II)

and reacting said compound of formula II with a compound that converts the —OH substituent into the radical of formula —OSO$_2$—$R^3$.

The reduction of a compound of formula III is said to be enantioselective if the optical yield is 60% or more, preferably 70% or more, most preferably 80% or more. The predominance of a configuration at the carbon atom indicated by an asterisk therefore refers in formula II to enantiomer ratios of at least 80:20, preferably of at least 85:15 and, most preferably, of at least 90:10, with the R or S form predominating.

The enantio-selective reduction is carried out in a manner known per se. The platinum catalysts employed are applied to inert carriers, e.g. to carbon, alumina, calcium carbonate or barium sulfate, with alumina being the preferred carrier. The catalysts are activated in known manner with hydrogen at 200°–400° C. and then modified (impregnated) with a solution of a cinchona alkaloid and/or a cinchona alkaloid is added direct during the reduction. Cinchona alkaloids will be understood as meaning the group of quinoline plant bases that can be isolated principally from the bark of trees of the species cinchona and remijia. They comprise in particular the alkaloids (−)-quinine, (+)-quinidine, (+)-cinchonine and (−)-cinchonidine. The use of (−)-quinine and (−)-cinchonidine leads to compounds of formula II in the R form, whereas compounds of formula II in the S form are obtained with (+)-quinidine and (+)-cinchonine. It is preferred to use (−)-cinchonidine. Suitably, the hydrogenation takes place in a pressure reactor such as an autoclave under a hydrogen pressure of 10 to 170 bar, preferably of 50 to 150 bar, and at room temperature ±30° C., preferably in the range from 0° to 30° C. Preferred solvents for the impregnation are those that dissolve the cinchona alkaloid employed, in particular $C_1$–$C_7$alkanols such as ethanol, or ethers such as tetrahydrofuran. Examples of suitable solvents for the hydrogenation are aromatic hydrocarbons such as benzene or toluene, and also halogenated hydrocarbons such as dichloromethane, ethers such as tert-butyl methyl ether, or low boiling carboxylates such as ethyl acetate.

As may be inferred from the definition of the asterisk in formula II, the compounds of formula II can be obtained in the above described manner in optical yields of at least 60%, preferably 70% and, most preferably, at least 80%. In the course of the further reaactin to sulfonic acid esters of formula I as described above, the optical yield can be increased such that compounds of formula I are obtained in substantially pure form, i.e. in optical yields of at least 95%, preferably of at least 97.5% and, most preferably, of at least 99 to 100%.

The compounds of formula I are valuable intermediates for the preparation of ACE inhibitors or precursors thereof. This class of compound has met with increasing interest in recent years. It extends the potential of available antihypertensives and thus the therapeutic possibilities of combating hypertension. In numerous effective ACE inhibitors (q.v. for example European patent application Nos. 50 850 and 72 352), importance attaches to the structural unit of the partial formula IV

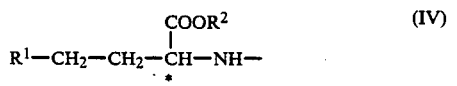

wherein $R^1$ and $R^2$ are as defined for formula I and the asterisk denotes a carbon atom in the S configuration.

The bond between the nitrogen atom of the partial formula IV and the adjacent carbon atom has been formed by the hitherto known processes for example by reacting a compound of formula III, under conditions of reductive alkylation, with a primary or secondary amine (reaction 1)

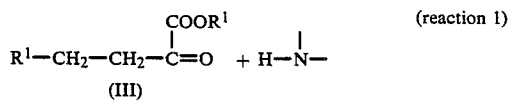

or by using an α-bromo ester of formula Va (reaction 2)

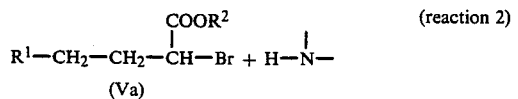

or by using an unsaturated compound of formula Vb (reaction 3)

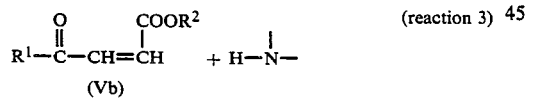

wherein $R^1$ and $R^2$ are as defined above.

In reactions 1 and 2, the desired compounds having the S configurtion of partial formula IV cannot be obtained direct. Instead, the racemic mixture obtained must be separated, resulting in a loss of at least 50% of said mixture. As the nitrogen atom of partial formula IV is usually itself the constituent of a complex chiral molecule at the time when reaction 1 or 2 takes place, a product loss of at least 50% in this late stage of the total synthesis of an ACE inhibitor must be regarded as unacceptable.

Although in reaction 3 it is possible to obtain a somewhat better ratio of isomers than that of a racemate, viz. up to 2:1, it is nevertheless necessary to carry out an additional reaction step, i.e a reduction.

The use of compounds of formula I in the process of the present invention obviates the shortcomings referred to above. In this process, starting from compounds of formula III, it is possible to obtain compounds containing the partial formula IV in chemical yields of more than 50%.

Specifically, the advantage of using compounds of formula I derives from the fact that, inter alia, the compounds of formula I can be reacted with primary or secondary amines without any appreciable racemisation or formation of elimination products. Thus compounds containing the partial formula IV are obtained in high chemical and optical yield, with inversion, by using compounds of formula I in which the asterisk denotes a carbon atom that is present in the preponderant number of molecules in the R configuration. In the same way, starting from compounds of formula I in which the asterisk denotes a carbon atom that is present in the preponderant number of molecules in the S configuration, it is possible to obtain compounds containing a structure corresponding to the partial formula IV, wherein the asterisk denotes a carbon atom that is in the R configuration.

This result is unexpected and surprising, as the prior art would lead one to expect secondary reactions and racemisation, both of which would cause the chemical yields to fall appreciably below 50%.

F. Effenberger et al., Angew. Chem. 95, 50, (1983), describes a leaving group that is suitable for synthesising N-substituted α-amino acids without racemisation, starting from α-hydroxycarboxylates. This leaving group is the α-trifluoromethanesulfonyloxy group. However, in the same publication, the authors advise against using other leaving groups, as the use of α-methanesulfonyloxycarboxylic acid derivatives and α-toluenesulfonyloxycarboxylic acid derivatives results in the formation, inter alia, of racemisation and elimination products owing to drastic reaction conditions. Further, the use of ethyl esters of α-bromo-, α-methanesulfonyloxy-, α-toluenesulfonyloxy- and α-chloropropionic acid gives yields of 40, 10, 5 and 1% respectively after 22 hours, whereas the reaction with the proposed α-trifluoromethanesulfonyloxy compound is 100% after 20 minutes.

Aside from the essentially unexpected result that aromatic sulfonyloxy compounds are admirably suitable for synthesising α-amino acids without racemisation, the compounds containing the radical $R^3$ employed in the process of this invention have lasting advantages compared with the known prior art compounds containing the $CF_3SO_2$—O— group; they are appreciably cheaper, ecologically safer and very much less toxic.

In a further aspect, the present invention therefore relates to the use of compounds of formula I for the preparation of compounds of formula VI

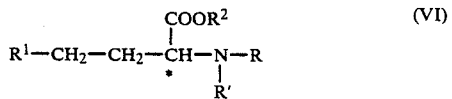

which comprises alkylating a compound of formula VII

with inversion, with a compound of formula I

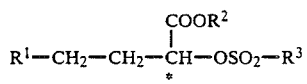

wherein $R^1$, $R^2$ and $R^3$ are as defined above, the asterisk denotes a carbon atom that is present either in the preponderant number of molecules in the S configuration or in the preponderant number of molecules in the R configuration, and R' is hydrogen or $C_1$-$C_7$alkyl and R is the radical of partial formula VIII

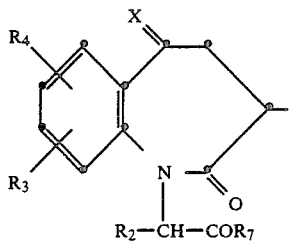

wherein $R_2$, $R_3$, $R_4$, $R_7$ (with dropped indices) and X are as defined in European patent application No. 72 352, or wherein R' is hydrogen or $C_1$-$C_7$alkyl and R is the radical of partial formula IX

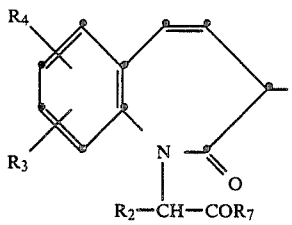

wherein $R_2$, $R_3$, $R_4$ and $R_7$ are as defined in European patent application No. 72 352, or wherein R' is hydrogen and R is 1-$C_1$-$C_7$aralkyl, or wherein R' and R are hydrogen.

The meanings of the substituents of partial formula VIII or IX in European patent application No. 72 352 are hydrogen or lower alkyl for $R_2$, and for $R_3$ and $R_4$, independently of each other, are hydrogen, lower alkyl, lower alkoxy, lower alkanoyloxy, hydroxy, halogen or trifluoromethyl, or $R_3$ and $R_4$ together are lower alkylenedioxy, $R_7$ together with the carbonyl group to which it is attached is carboxy or a functionally modified carboxyl group $CDR_7$, and X is oxo, two hydrogen atoms or a hydrogen atom together with a hydroxyl group. The term "lower" denotes organic radicals or compounds that contain up to 7, preferably up to 4 and, most preferably, 1 or 2, carbon atoms. More specific definitions will be found by referring to the patent application in question.

The above reaction, a substitutive alkylation, is carried out under customary general conditions in the temperature range from about 0° C. to the boiling point of the reaction mixture, preferably in the range from room temperature to about 100° C. The reaction advantageously takes place in the presence of a solvent that is inert to the reactants, e.g. in the presence of a chlorinated lower alkane such as chloroform or methylene chloride, of an acyclic or cyclic ether such as diethyl ether, 1,2-dimethoxyethane, dioxane or tetrahydrofuran, of a lower alkane carbonitrile such as acetonitrile, of a low boiling lower alkyl ester of a lower alkanoic acid, e.g. ethyl acetate, or of a tertiary amide of low molecular weight, e.g. N,N-dimethylformamide, N,N-dimethylacetamide, N-methylpyrrolidone, N-ethylpiperidone and hexamethylphosphoramide. It is advantageous to neutralize the strong acid $HOSO_2$-$R^3$ formed during the reaction by adding an acid acceptor, preferably an inorganic base such as a bicarbonate, carbonate or hydroxide of an alkali metal, an organic quaternary ammoniumsalt, e.g. a tetrabutylammonium salt, or an organic tertiary base such as triethylamine, N-ethylpiperidine, N-methylmorpholine, pyridine or quinoline.

This reaction proceeds with inversion, i.e. it is stereochemically uniform, such that the configuration at the carbon atom indicated by the asterisk is inverted. If therefore in a compound of formula I the asterisk indicates a carbon atom that is present in the preponderant number of molecules in the R configuration, the asterisk will then indicate in the compound of formula VI obtained from this compound of formula I a carbon atom that is present in the preponderant number of molecules in the S configuration, and vice versa. The expression "in the preponderant number of molecules in one configuration" with respect to formula VI has the same meaning as that given for formula I. If R and R' in formula VII are hydrogen, i.e. if a compound of formula I is reacted with ammonia, the reaction will preferably be carried out under elevated pressure, e.g. at 10 to 20 bar, in an inert solvent such as acetonitrile.

The starting compounds of formula VII are known or can be prepared in a manner known per se (q.v. for example European patent application No. 72 352). The compounds of formula VI are either ACE inhibitors of formula VIa

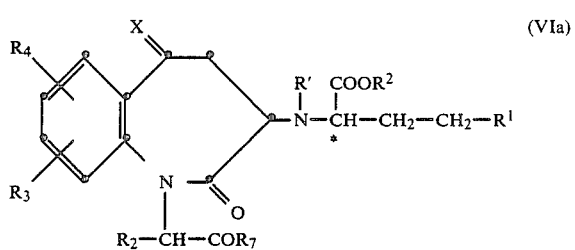

wherein $R^1$, $R^2$, R', the asterisk and $R_2$, $R_3$, $R_4$, $R_7$ and X are as defined above, or they are compounds of formula VIb

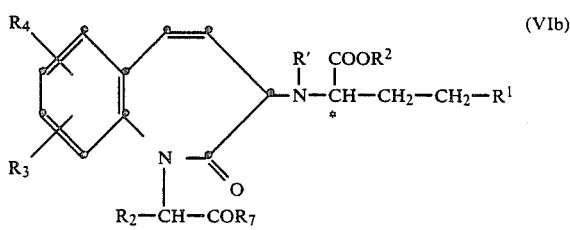

wherein $R^1$, $R^2$, R', the asterisk and $R_2$, $R_3$, $R_4$ and $R_7$ are as defined above, or they are precursors of ACE inhibitors of formula VIc

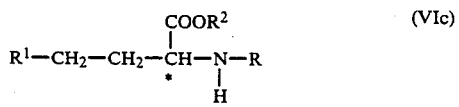

wherein $R^1$, $R^2$ and the asterisk are as defined above and R is 1-$C_1$-$C_7$aralkyl, e.g. benzyl, 1-phenylethyl or 1-naphthylethyl or, if R is hydrogen, they are precursors of ACE inhibitors of formula VId

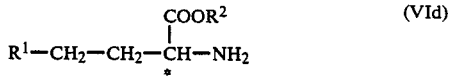

wherein $R^1$, $R^2$ and the asterisk are as defined above.

Compounds of formula VIb can be converted in a manner known per se by reduction (hydrogenolysis) into compounds of formula VIa, wherein X denotes 2 hydrogen atoms. This process is especially advantageous, and is therefore preferred, if in a compound of formula VIb $R_7$ is 1-$C_1$-$C_7$aralkoxy, e.g. benzyloxy, as in this event the reduction of the C—C double bond and the conversion of a benzyloxycarbonyl group $COR_7$ into the carbonyl group $COR_7$ can be carried out simultaneously.

Aside from the direct route (compound of formula I+ammonia), compounds of formula VId are also obtainable by a two-step route without adversely affecting on the chemical or optical yield. Thus compounds of formula VIc can be converted into compounds of formula VId in a manner known per se, under mild conditions (hydrogenolysis), thereby retaining the configuration at the carbon atom indicated by the asterisk.

The amino acid esters of formula VId are in turn suitable for use as essential components for synthesising ACE inhibitors, as they are able to contain the important structural unit of partial formula IV.

To sum up, the novel compounds of formula I prove to be key compounds for synthesising ACE inhibitors whether by the direct route of I to VIa, by the route of I via VIb to VIa, or by the route starting from I via VId, in which case resultant compounds of formula VIc may be processed direct without isolation. The synthesis is distinguished by high chemical and optical yields.

The invention is illustrated by the following non-limitative Examples. The percentages additionally qualified by "ee" denote optical yields. Temperatures are given in degrees centigrade.

EXAMPLE 1

The preparation of the catalyst and the hydrogenation may be carried out in accordance with the particulars of U.S. Pat. No. 4,329,487:

Preparation of the catalyst: 1 g of 5% Pt/C (e.g. Degussa Type F 101 R) is heated to 300° C. for 3 hours in a weak stream of hydrogen. After cooling under argon, the catalyst is refluxed in 80 ml of a 1% ethanolic solution of cinchonidine, isolated by filtration, washed with a small quantity of ethanol and subsequently with the solvent employed for the hydrogenation.

Hydrogenation: 20 g of ethyl 4-phenyl-2-oxobutyrate are dissolved in 100 ml of benzene and flushed in a 300 ml autoclave equipped with an aerating stirrer. Then 0.1 g of cinchonitidine and the prepared catalyst are added and the hydrogenation is carried out in conventional manner at 150 bar and 20°-30° C. When hydrogen absorption is terminated, the catalyst is isolated by filtration and the solvent is removed on a rotary evaporator. The chemical yield of ethyl 2-hydroxy-4-phenylbutyrate is c. 95% and the optical yield of the R form is 70%.

EXAMPLE 2

The procedure of Example 1 is repeated, using 1 g of 5% Pt/Al$_2$O$_3$ (e.g. Engelhard Type 4759 b) and carrying out the hydrogenation for 2 hours at 400° C. The chemical yield is c. 95% and the optical yield 72%.

EXAMPLE 3

The procedure of Example 2 is repeated, except that the the catalyst is not treated beforehand with a cinchonidine solution. The chemical yield is c. 95% and the optical yield 68%.

EXAMPLE 4

The procedure of Example 2 is repeated, but using the following solvents for the hydrogenation: (a) toluene, (b) dichloromethane, (c) ethyl acetate, (d) t-butyl methyl ether. The chemical yields are c. 95% and the optical yields are between 60 and 70%.

EXAMPLE 5

The reaction is carried out as in Example 3, but at a temperature of 5° C. The chemical yield is c. 95% and the optical yield 80%.

EXAMPLE 6

104.16 g of ethyl (—)-R-2-hydroxy-4-phenylbutyrate with $[\alpha]_D^{20} = -17.0°$ (82% ee) and 121.89 g of 4-nitrobenzenesulfonyl chloride are dissolved at room temperature in 500 ml of toluene. At 0° C., 66.8 g of triethylamine are added dropwise over 1 hour. The batch is then stirred for 1 hour at room temperature. After aqueous working up and extraction of the toluene phase with 1N hydrochloric acid, the combined toluene phases are filtered over a small amount of silica gel and concentrated on a rotary evaporator. The residual oil is taken up to 100 ml of a 4:1 mixture of cyclohexane/ethyl acetate and the solution is stirred for 48 hours at room temperature, then for 8 hours at 0° C., and finally filtered. The filter residue is dried and gives 41.5 g of racemic ethyl 2-(4-nitrobenzenesulfonyloxy)-4-phenylbutyrate of m.p. 68°-70° C. The filtrate is concentrated by evaporation on a rotary evaporator and degassed in a high vacuum at 45° C., affording 146.5 g of enriched ethyl (+)-R-2-(4-nitrobenzenesulfonyloxy)-4-phenylbutyrate with $[\alpha]_D^{20} = +10.6°$ (3%, abs. ethanol). The product so obtained has a 90% excess of enantiomers and is 95% pure according to HPLC.

Ethyl (+)-R-2-(4-nitrobenzenesulfonyloxy)-4-phenylbutyrate prepared from pure ethyl (—)-R-2-hydroxy-4-phenylbutyrate ($[\alpha]_D^{20} = -20.8°$, 1%, chloroform) according to the particulars of this Example has an angle of rotation $[\alpha]_D^{20} = +13.2°$ (3%, abs. ethanol).

EXAMPLE 7

Following the procedure of Example 6, the corresponding ethyl (—)-R-2-(2-nitrobenzenesulfonyloxy)-4-phenylbutyrate is prepared from ethyl (—)-R-2-hydroxy-4-phenylbutyrate (82% ee) with 2-nitrobenzenesulfonyl chloride. The ester obtained as an oil in 95% yield has an angle of rotation $[\alpha]_D^{20} = -9.6°$ (3%, abs. ethanol).

EXAMPLE 8

Following the procedure of Example 6, ethyl (+)-R-2-(3-nitrobenzenesulfonyloxy)-4-phenylbutyrate is prepared from ethyl (−)-R-2-hydroxy-4-phenylbutyrate (82% ee) with 3-nitrobenzenesulfonyl chloride. The product has an angle of rotation $[\alpha]_D^{20} = +6.2°$ (3%, abs. ethanol).

EXAMPLE 9

Following the procedure of Example 6, ethyl (−)-R-2-(pentafluorobenzenesulfonyloxy)-4-phenylbutyrate of m.p. 64°–65° C. (crystallisation from ether/cyclohexane) is obtained in 98% yield from ethyl (−)-R-2-hydroxy-4-phenylbutyrate (84% ee) with pentafluorobenzenesulfonyl chloride. The product has an angle of rotation $[\alpha]_D^{20} = -2.5° \pm 0.2°$; $\alpha_{436}^{20} = -12.4°$ (5%, chloroform).

EXAMPLE 10

Following the procedure of Example 6, ethyl (−)-R-2-(2,4-dinitrobenzenesulfonyloxy)-4-phenylbutyrate is obtained as an oil in 95% yield from ethyl (−)-R-2-hydroxy-4-phenylbutyrate (100% ee) with 2,4-dinitrobenzenesulfonylchloride. The oil is crystallised from a 1:4 mixture of ethyl acetate/cyclohexane and gives an almost white crystalline solid in 83.7% yield; m.p. 69°–71° C.; $[\alpha]_D^{20} = -10.6°$ (3%, abs. ethanol).

EXAMPLE 11

393.4 g of enriched ethyl (+)-R-2-(4-nitrobenzenesulfonyloxy)-4-phenylbutyrate (90% ee) are dissolved in 600 ml of acetonitrile and to the solution are added 121.4 g of triethylamine at room temperature. After heating to 70° C., 210 g of (+)-R-1-phenylethylamine are added over 2 hours. The reaction mixture is then stirred for 16 hours at 70° C. When the reaction is complete, the mixture is cooled, precipitated ammonium salt is removed by filtration and the filtrate is concentrated by evaporation. The residue is partitioned between water and dichloromethane and the aqueous phase is adjusted to pH 6 with 2N hydrochloric acid. The combined organic phases are concentrated on a rotary evaporator and the residual oil is subsequently dissolved in a mixture of 1000 ml of diethyl ether and 250 ml of dichloromethane and the resultant solution is saturated, with stirring, with gaseous hydrogen chloride. The precipitated crystalline suspension is diluted at 0° C. with 700 ml of cyclohexane and filtered at −12° C. The filter product is washed with cyclohexane and dried to constant weight in a high vacuum. The yield is 287.5 g. The ratio of diastereoisomers determined by HPLC is SR:SS=98.5:1.5. One recrystallisation gives N-(R-1-phenylethyl)-S-homophenylaniline ethyl ester hydrochloride as pure SR isomer. Melting point: 181.5°–182.5° C; $[\alpha]_D^{20} = +52.5°$ (1%, methanol).

EXAMPLE 12

86.88 g of N-(R-1-phenylethyl)-S-homophenylalanine ethyl ester hydrochloride with an angle of rotation of +52.5° are dissolved in 870 ml of ethanol and 87 ml of deionized water and the solution is hydrogenated with 17 g of Pd/C (5%) under normal pressure for 1 hour. The hydrogenation is discontinued after a hydrogen absorption of 109%. After filtration, the filtrate is concentrated to a volume of c. 200 ml. With stirring, 750 ml of diethyl ether are added dropwise and the resultant crystalline suspension is cooled to 0° C. and filtered. The filter product is washed with ice-cold ether and dried in a high vacuum, affording 55.23 g of (+)-S-homophenylalanine ethyl ester hydrochloride with an angle of rotation of $[\alpha]_D^{20} = +41.1°$ (1%, ethanol). A further 3.96 g of product is obtained in comparable purity from the mother liquor by concentration.

EXAMPLE 13

A concentrated ethanolic hydrogenation solution (0.7 molar batch) from Example 12 is diluted with 500 ml of methanol and stirred at room temperature with a solution of 58.8 g of sodium hydroxide and 58.8 g of water. Precipitated sodium chloride is removed by filtration and the filtrate is concentrated to a volume of c. 300 ml, whereupon homophenylalanine sodium salt begins to precipitate. The crystallisation is brought to completion by the dropwise addition of 1000 ml of acetonitrile, with stirring and subsequent cooling to 0° C. The product is isolated by filtration, washed with cold acetonitrile and dried to constant weight in a high vacuum. The isolated sodium salt has an angle of rotation $[\alpha]_D^{20} = +37.2°$ (1%, 1N hydrochloric acid).

EXAMPLE 14

10.0 g of homophenylalanine sodium salt are dissolved in 60 ml of deionised water and the solution is added dropwise over 1 hour to 24 ml of 2N hydrochloric acid to form a white, faintly lustrous crystalline suspension. This suspension is adjusted with 1N sodium hydroxide solution to pH 4.0 and then stirred for 2 hours at room temperature and filtered. The filter product is washed with deionised water and dried at room temperature in a high vacuum, affording pure (+)-S-homophenylalanine with an angle of rotation of $[\alpha]_D^{20} = +45.6°$ (1%, 1N hydrochloric acid). Melting point: 287°–290° C. Yield: 89.6%.

EXAMPLE 15

In an autoclave, 78.7 g of ethyl (+)-R-2-(4-nitrobenzenesulfonyloxy)-4-phenylbutyrate are added to 40 ml of acetonitrile and brought to reaction with 7.5 g of ammonia at 60° C. under a pressure of 12–18 bar. The reaction is complete after 6 to 7 hours. The reaction solution is concentrated by evaporation and the residue is taken up in 200 ml of diethyl ether. To the ethereal solution is added 130 ml of hydrochloric acid in ethyl acetate (1.7N), whereupon almost white crystalline (+)-S-homophenylalanine ethyl ester with an angle of rotation of $[\alpha]_D^{20} = +37.8°$ precipitates. Yield: 95.6%. An angle of rotation of +37.8° (1%, ethanol) corresponds to 93% ee.

EXAMPLE 16

1-Carboxymethyl-3S-[(1S-ethoxycarbonyl-3-phenyl-propyl)amino]-2,3,4,5-tetrahydro-1H-[1]-benzapin-2-one 46.1 g of 1-tert-butoxycarbonylmethyl-3S-amino-2,3,4,5-tetrahydro-1H-(1)-benzazepin-2-one, 84.3 g of ethyl (+)-R-2-(4-nitrobenzenesulfonyloxy)-4-phenylbutyrate (enriched to 90% ee) and 19.53 g of N-methylmorpholine are reacted, without a solvent, at 75°–80° C. for 9 hours. The precipitated N-methylmorpholine salt of 4-nitrobenzenesulfonic acid is dissolved by addition of 250 ml of ethyl acetate and 150 ml of water. The pH is adjusted to 8.8 with c. 150 ml of 2N sodium carbonate solution and the ethyl acetate phase is separated and washed twice with water. Analysis by HPLC shows that the residual oil (98 g) obtained after distilling off the ethyl acetate has a diastereoisomer ratio of SS:SR=96:4.

The preparation of the crude product is effected by introducing 54 g of gaseous hydrogen chloride into a solution of 96 g of the above oil in 200 ml of ethyl acetate at 0°–10° C. After complete solvolysis of the tert-butyl ester, the crude product is obtained as a finely crystalline suspension. Excess hydrogen chloride is completely removed by repeatedly distilling off ethyl acetate in vacuo. The highly concentrated crystalline suspension is then diluted with 200 ml of acetone and filtered at 15° C. The filter cake is washed with two 50 ml portions of ethyl acetate and dried to constant weight in vacuo at 60° C., affording 62.5 g (85.4%) of almost white product with a diastereoisomer ratio of SS:SR=99.1:0.9. For further purification, these 62.5 g of crude product are suspended in 250 ml of ethyl acetate and the suspension is heated for 6 hours under reflux and filtered at 15° C. The filter product is washed and dried at 60° C. in a high vacuum. Yield: 61.15 g (83.6%). Ratio of SS:SR=99.7:0.3; $[\alpha]_D^{20} = -137.3°$ (1%, abs. ethanol); m.p. 181° C.

We claim:

1. A compound of the formula

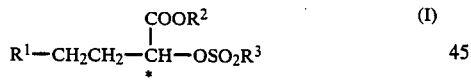

wherein
- $R^1$ is (a) $C_{5-6}$ cycloalkyl which is unsubstituted or substituted by $C_{1-7}$ alkyl or (b) phenyl which is unsubstituted or substituted by at least one substituent selected from $C_{1-7}$ alkyl, hydroxy, $C_{1-7}$ alkoxy, $C_{1-7}$ alkanoyloxy, fluorine, $C_{1-7}$ alkylenedioxy, amino, $C_{1-7}$ alkylamino, di($C_{1-7}$ alkyl)amino, $C_{1-7}$ alkanoylamino, carbamoyl, $C_{1-7}$ alkyl carbamoyl, di($C_{1-7}$ alkyl) carbamoyl, $C_{1-7}$ alkylsulfonylamino, sulfamoyl, $C_{1-7}$ alkylsulfamoyl, di($C_{1-7}$ alkyl)sulfamoyl, $C_{1-7}$ haloalkyl, $C_{1-7}$ hydroxyalkyl, and $C_{1-7}$ aminoalkyl;
- $R^2$ is $C_{1-7}$ alkyl;
- $R^3$ is phenyl which is substituted by halogen or nitro; and the asterisk denotes a carbon atom that is either present in the preponderant number of molecules in the S configuration or in the preponderant number of molecules in the R configuration.

2. A compound of formula I according to claim 1, wherein $R^2$, $R^3$ and the asterisk are as defined in claim 1 and $R^1$ is $C_5$-$C_6$cycloalkyl, phenyl or phenyl which is substituted by $C_1$-$C_7$alkyl, hydroxy, $C_1$-$C_7$alkoxy, $C_1$-$C_7$alkanoyloxy, fluorine, trifluoromethyl or $C_1$-$C_7$-alkylenedioxy.

3. A compound of formula I according to claim 1, wherein $R^1$ is $C_5$-$C_6$cycloalkyl, phenyl or phenyl which is substituted by a member selected from $C_1$-$C_4$alkyl, hydroxy, $C_1$-$C_4$alkoxy or fluorine, $R^2$ is $C_1$-$C_4$alkyl, $R^3$ is 2-, 3- or 4-nitrophenyl, 2,4-dinitrophenyl or pentafluorophenyl, and the asterisk denotes a carbon atom that is either present in the preponderant number of molecules in the S configuration or in the preponderant number of molecules in the R configuration.

4. A compound of formula I according to claim 1, wherein $R^1$ is cyclohexyl, phenyl, $C_1$-$C_4$alkylphenyl or $C_1$-$C_4$alkoxyphenyl, $R^2$ is $C_1$-$C_4$alkyl, $R^3$ is 4-nitrophenyl or 2,4-dinitrophenyl, and the asterisk denotes a carbon atom that is present in the preponderant number of molecules in the R-configuration.

5. A compound of formula I according to claim 1, wherein $R^1$ is phenyl, $R^2$ is $C_1$-$C_4$alkyl, $R^3$ is 4-nitrophenyl or 2,4-dinitrophenyl and the asterisk denotes a carbon atom that is present in the preponderant number of molecules in the R configuration.

6. A compound according to claim 1 being ethyl (+)-R-2-(4-nitrobenzenesulfonyloxy)-4-phenylbutyrate or ethyl (−)-R-2-(2,4-dinitrobenzenesulfonyloxy)-4-phenylbutyrate.

7. A process for the preparation of a compound of the formula

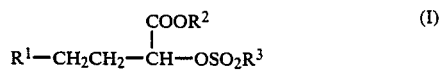

wherein
- $R^1$ is (a) $C_{5-6}$ cycloalkyl which is unsubstituted or substituted by $C_{1-7}$ alkyl or (b) phenyl which is unsubstituted or substituted by at least one substituent selected from $C_{1-7}$ alkyl, hydroxy, $C_{1-7}$ alkoxy, $C_{1-7}$ alkanoyloxy, fluorine, $C_{1-7}$ alkylenedioxy, amino, $C_{1-7}$ alkylamino, di($C_{1-7}$ alkyl)amino, $C_{1-7}$ alkanoylamino, carbamoyl, $C_{1-7}$ alkyl carbamoyl, di($C_{1-7}$ alkyl) carbamoyl, $C_{1-7}$ alkylsulfonylamino, sulfamoyl, $C_{1-7}$ alkylsulfamoyl, di($C_{1-7}$ alkyl)sulfamoyl, $C_{1-7}$ haloalkyl, $C_{1-7}$ hydroxyalkyl, and $C_{1-7}$ aminoalkyl;
- $R^2$ is $C_{1-7}$ alkyl;
- $R^3$ is phenyl which is substituted by halogen or nitro; and the asterisk denotes a carbon atom that is either present in the preponderant number of molecules in the S configuration or in the preponderant number of molecules in the R configuration which comprises reacting an alpha-hydroxy ester of the formula

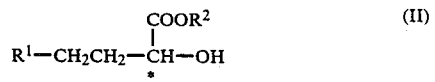

wherein $R^1$, $R^2$ and the asterisk are as defined above, with an $R^3$-sulfonic acid anhydride or $R^3$-sulfonyl-halide wherein $R^3$ is as defined above.

8. The process of claim 7 wherein said sulfonic acid anhydride is

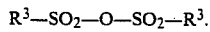

9. A process for the preparation of a compound of the formula

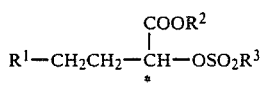  (I)

wherein
R¹ is (a) $C_{5-6}$ cycloalkyl which is unsubstituted or substituted by $C_{1-7}$ alkyl or (b) phenyl which is unsubstituted or substituted by at least one substituent selected from $C_{1-7}$ alkyl, hydroxy, $C_{1-7}$ alkoxy, $C_{1-7}$ alkanoyloxy, fluorine, $C_{1-7}$ alkylenedioxy, amino, $C_{1-7}$ alkylamino, di($C_{1-7}$ alkyl)amino, $C_{1-7}$ alkanoylamino, carbamoyl, $C_{1-7}$ alkyl carbamoyl, di($C_{1-7}$ alkyl) carbamoyl, $C_{1-7}$ alkylsulfonylamino, sulfamoyl, $C_{1-7}$ alkylsulfamoyl, di($C_{1-7}$ alkyl)sulfamoyl, $C_{1-7}$ haloalkyl, $C_{1-7}$ hydroxyalkyl, and $C_{1-7}$ aminoalkyl;
$R^2$ is $C_{1-7}$ alkyl;
$R^3$ is phenyl which is substituted by halogen or nitro; and the asterisk denotes a carbon atom that is either present in the preponderant number of molecules in the S configuration or in the preponderant number of molecules in the R configuration comprising enantio-selectively reducing a compound of the formula

  (III)

in the presence of (a) a platinum catalyst on a carrier and (b) a cinchona alkaloid, to a compound of the formula

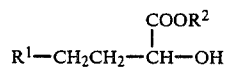  (II)

and reacting said compound of formula II with an $R^3$-sulfonyl-anhydride or an $R^3$-sulfonyl-halide.

10. A process for the preparation of a compound of the formula

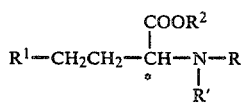  (VI)

wherein
R¹ is (a) $C_{5-6}$ cycloalkyl which is unsubstituted or substituted by $C_{1-7}$ alkyl or (b) phenyl which is unsubstituted or substituted by at least one substituent selected from $C_{1-7}$ alkyl, hydroxy, $C_{1-7}$ alkoxy, $C_{1-7}$ alkanoyloxy, fluorine, $C_{1-7}$ alkylenedioxy, amino, $C_{1-7}$ alkylamino, di($C_{1-7}$ alkyl)amino, $C_{1-7}$ alkanoylamino, carbamoyl, $C_{1-7}$ alkyl carbamoyl, di($C_{1-7}$ alkyl) carbamoyl, $C_{1-7}$ alkylsulfonylamino, sulfamoyl, $C_{1-7}$ alkylsulfamoyl, di($C_{1-7}$ alkyl)sulfamoyl, $C_{1-7}$ haloalkyl, $C_{1-7}$ hydroxyalkyl, and $C_{1-7}$ aminoalkyl;
$R^2$ is $C_{1-7}$ alkyl;
and the asterisk denotes a carbon atom that is either present in the preponderant number of molecules in the S configuration or in the preponderant number of molecules in the R configuration; and
(i) R' is hydrogen or $C_{1-7}$ alkyl; and R is a group of the formulae

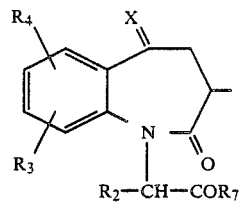  (VIII)

or

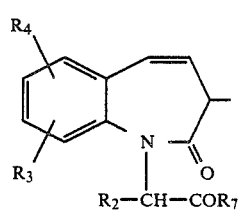  (IX)

or (ii) R' is hydrogen and R is hydrogen; 1-phenyl $C_{1-7}$ alkyl or 1-naphthyl-$C_{1-7}$ alkyl; in which
$R_2$ is hydrogen or $C_{1-7}$ alkyl;
$R_3$ and $R_4$ are each independently hydrogen, $C_{1-7}$ alkyl, $C_{1-7}$ alkoxy, $C_{1-7}$ alkanoyloxy, hydroxy, halogen, or trifluoromethyl or both $R_3$ and $R_4$ together are $C_{1-7}$ alkylenedioxy;
$R_7$ together with the carbonyl group to which it is attached is carboxy or a functionally modified carboxy; and
X is oxo, two hydrogen atoms, or one hydrogen atom and one hydroxyl group which comprises alkylating a compound of the formula

  (II)

under inversion, with a compound of the formula

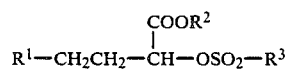  (I)

wherein R', R, $R^1$, $R^2$ and the asterisk are as defined above and $R^3$ is phenyl which is substituted by halogen or nitro.

11. The process of claim 10 wherein the compound of formula VI is

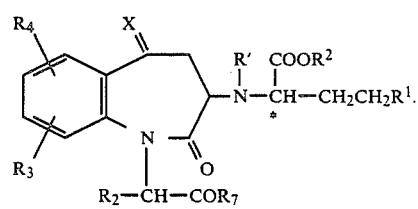  (VIa)

12. The process of claim 10 wherein the compound of formula VI is

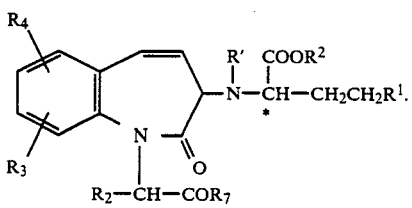

(VIb)

13. A process of converting a compound of the formula

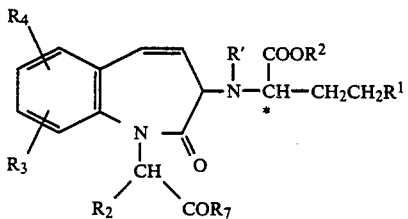

(VIb)

into a compound of the formula

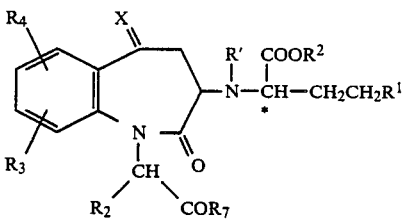

(VIa)

wherein

R$^1$ is (a) C$_{5-6}$ cycloalkyl which is unsubstituted or substituted by C$_{1-7}$ alkyl or (b) phenyl which is unsubstituted or substituted by at least one substituent selected from C$_{1-7}$ alkyl, hydroxy, C$_{1-7}$ alkoxy, C$_{1-7}$ alkanoyloxy, fluorine, C$_{1-7}$ alkylenedioxy, amino, C$_{1-7}$ alkylamino, di(C$_{1-7}$ alkyl)amino, C$_{1-7}$ alkanoylamino, carbamoyl, C$_{1-7}$ alkyl carbamoyl, di(C$_{1-7}$ alkyl) carbamoyl, C$_{1-7}$ alkylsulfonylamino, sulfamoyl, C$_{1-7}$ alkylsulfamoyl, di(C$_{1-7}$ alkyl)sulfamoyl, C$_{1-7}$ haloalkyl, C$_{1-7}$ hydroxyalkyl, and C$_{1-7}$ aminoalkyl;

R$^2$ is C$_{1-7}$ alkyl; the asterisk denotes a carbon atom that is either present in the preponderant number of molecules in the S configuration or in the preponderant number of molecules in the R configuration;

R' is hydrogen or C$_{1-7}$ alkyl;

R$_2$ is hydrogen or C$_{1-7}$ alkyl;

R$_3$ and R$_4$ are each independently hydrogen, C$_{1-7}$ alkyl, C$_{1-7}$ alkoxy, C$_{1-7}$ alkanoyloxy, hydroxy, halogen, or CF$_3$ or both R$_3$ and R$_4$ together are C$_{1-7}$ alkylene dioxy;

R$_7$ together with the carbonyl group to which it is attached is carboxy or functionally modified carboxy; and X is two hydrogens, comprising hydrogenolysing said compounds of formula VIb.

14. The process of claim 10 wherein R$^1$ is hydrogen and R is 1-phenyl-C$_{1-7}$ alkyl or 1-naphthyl-C$_{1-7}$ alkyl.

15. The process of claim 10 wherein R and R' are each hydrogen.

16. The process of claim 7 wherein 3-nitrobenzensulfonyl halide is used as said R$^3$-sulfonyl compound.

17. A process according to claim 7, wherein an R$^3$-sulfonic acid anhydride is used as said R$^3$-sulfonyl compound.

18. A process according to claim 7, wherein an R$^3$-sulfonyl halide is used as said R$^3$-sulfonyl compound.

19. A process according to claim 7, wherein a 4-nitrobenzenesulfonyl halide is used as said R$^3$-sulfonyl compound.

20. A process according to claim 7, wherein a 2,4-dinitrobenezenesulfonyl halide is used as said R$^3$-sulfonyl compound.

21. A process according to claim 7, wherein a pentafluorobenzenesulfonyl halide is used as said R$^3$-sulfonyl compound.

22. A process according to claim 9, wherein the carrier is carbon, alumina, calcium carbonate or barium sulfate.

23. A process according to claim 9, wherein the cinchona alkaloid is (−)-quinine, (+)-quinidine, (+)-cinchonine or (−)-cinchonidine.

24. A process according to claim 9, wherein the cinchona alkaloid is (−)-cinchonidine.

25. A process according to claim 9, wherein the starting material is ethyl 4-phenyl-2-oxobutyrate.

* * * * *

UNITED STATES PATENT AND TRADEMARK OFFICE
CERTIFICATE OF CORRECTION

PATENT NO. : 4,785,089
DATED : Nov. 15, 1988
INVENTOR(S) : Hans-Ulrich Blaser, Hans-Peter Jalett & Gottfried Sedelmeier It is certified that error appears in the above-identified patent and that said Letters Patent is hereby corrected as shown below:

In Claim 10, line 39 thereof " 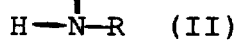 "

should read:

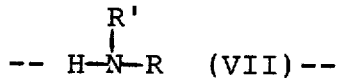

Signed and Sealed this

Twenty-sixth Day of December, 1989

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,785,089
DATED : November 15, 1988
INVENTOR(S) : Blaser et al.

It is certified that error appears in the above—identified patent and that said Letters Patent is hereby corrected as shown below:

In claim 14, line 1 thereof,

"$R^1$" should read --R'--.

Signed and Sealed this

Fifteenth Day of January, 1991

Attest:

HARRY F. MANBECK, JR.

Attesting Officer    Commissioner of Patents and Trademarks